(12) United States Patent
Macinga et al.

(10) Patent No.: US 10,271,548 B2
(45) Date of Patent: *Apr. 30, 2019

(54) METHODS AND COMPOSITIONS FOR USE WITH GEL DISPENSERS

(71) Applicant: GOJO Industries, Inc., Akron, OH (US)

(72) Inventors: David R. Macinga, Stow, OH (US); Sarah L. Edmonds, Canal Fulton, OH (US); Kristin E. Hartzell, Massillon, OH (US); Kelly A. Dobos, Cincinnati, OH (US); Carol A. Quezada, Canal Fulton, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/893,817

(22) Filed: Feb. 12, 2018

(65) Prior Publication Data

US 2018/0160680 A1 Jun. 14, 2018

Related U.S. Application Data

(63) Continuation of application No. 15/198,083, filed on Jun. 30, 2016, now Pat. No. 10,004,227, which is a continuation of application No. 12/814,527, filed on Jun. 14, 2010, now Pat. No. 9,402,393.

(60) Provisional application No. 61/187,041, filed on Jun. 15, 2009.

(51) Int. Cl.

| A61K 8/04 | (2006.01) |
|---|---|
| A61K 8/34 | (2006.01) |
| A61K 8/81 | (2006.01) |
| A01N 25/04 | (2006.01) |
| A01N 25/16 | (2006.01) |
| A01N 25/30 | (2006.01) |
| A01N 31/02 | (2006.01) |
| A61Q 19/00 | (2006.01) |
| A61Q 19/10 | (2006.01) |
| B05B 11/00 | (2006.01) |

(52) U.S. Cl.
CPC ............ *A01N 31/02* (2013.01); *A01N 25/16* (2013.01); *A61K 8/042* (2013.01); *A61K 8/34* (2013.01); *A61K 8/345* (2013.01); *A61K 8/8152* (2013.01); *A61Q 19/00* (2013.01); *A61Q 19/10* (2013.01); *B05B 11/30* (2013.01); *A61K 2800/48* (2013.01); *A61K 2800/5922* (2013.01); *A61K 2800/87* (2013.01)

(58) Field of Classification Search
CPC .... A01N 31/02; A01N 2300/00; A01N 25/04; A01N 25/16; A01N 25/30; A61K 2800/48; A61K 2800/5922; A61K 2800/87; A61K 8/042; A61K 8/34; A61K 8/345; A61K 8/8152; A61Q 19/00; A61Q 19/10; B05B 11/30

See application file for complete search history.

(56) References Cited

U.S. PATENT DOCUMENTS

| 3,069,319 | A | 12/1962 | Stearns |
|---|---|---|---|
| 3,954,960 | A | 5/1976 | Valan |
| 4,692,277 | A | 9/1987 | Siklosi |
| 4,933,177 | A | 6/1990 | Grollier et al. |
| 4,956,170 | A * | 9/1990 | Lee ............ A61K 8/042 |
| | | | 514/772.1 |
| 4,961,921 | A | 10/1990 | Chuang et al. |
| 5,167,950 | A | 12/1992 | Lins |
| 5,266,598 | A | 11/1993 | Ninomiya et al. |
| 5,340,570 | A | 8/1994 | Wong et al. |
| 5,714,135 | A | 2/1998 | Lee et al. |
| 5,968,204 | A | 10/1999 | Wise |
| 5,985,294 | A | 11/1999 | Peffly |
| 6,080,417 | A | 6/2000 | Kramer et al. |
| 6,096,297 | A | 8/2000 | Jones et al. |
| 6,096,349 | A | 8/2000 | Petri et al. |
| 6,123,953 | A * | 9/2000 | Greff ............ A01N 31/02 |
| | | | 424/401 |
| 6,221,922 | B1 | 4/2001 | Policello et al. |
| 6,793,914 | B2 | 9/2004 | Clarkson et al. |
| 6,846,352 | B2 * | 1/2005 | Yatake ............ C09D 11/40 |
| | | | 106/31.58 |
| 7,199,090 | B2 | 4/2007 | Koivisto et al. |
| 7,247,295 | B2 | 7/2007 | Schmaus et al. |
| 7,384,646 | B2 | 6/2008 | Koybayashi et al. |

(Continued)

FOREIGN PATENT DOCUMENTS

| AL | 9939687 A1 | 8/1999 |
|---|---|---|
| EP | 0796610 A1 | 9/1997 |

(Continued)

OTHER PUBLICATIONS

European Search Report for European Application No. EP10165683 dated Sep. 5, 2012; 6 pages.
International Search Report and Written Opinion of the International Searching Authority, International Appl No. PCT/US2008/081502 dated Dec. 16, 2010; 13 pages.
International Search Report for International Appl. No. PCT/US2010/038453 dated Feb. 23, 2011; 2 pages.
International Search Report on Patentability for International Appl. No. PCT/US10/38453 dated Dec. 16, 2011; 8 pages.

(Continued)

*Primary Examiner* — Michael B. Pallay
(74) *Attorney, Agent, or Firm* — Calfee, Halter & Griswold LLP

(57) ABSTRACT

A dispensable gel composition is provided. The dispensable gel composition includes a $C_{1-4}$ alcohol, a polyacrylate thickener, and a plug-preventing additive. The dispensable gel exhibits less misdirection during dispensing from a dispensing device than gel compositions that are otherwise identical, but for the presence of the plug-preventing additive.

11 Claims, No Drawings

(56) References Cited

U.S. PATENT DOCUMENTS

| | | |
|---|---|---|
| 7,537,652 B2 | 5/2009 | Koganehira et al. |
| 7,566,460 B2 | 7/2009 | Asmus et al. |
| 7,582,681 B2 | 9/2009 | Schmaus et al. |
| 7,632,871 B2 | 12/2009 | Kobayashi et al. |
| 9,402,393 B2 * | 8/2016 | Macinga ................ A01N 31/02 |
| 2004/0228820 A1 | 11/2004 | Elliott et al. |
| 2005/0222276 A1 | 10/2005 | Schmaus et al. |
| 2005/0228032 A1 | 10/2005 | Merianos et al. |
| 2007/0059331 A1 | 3/2007 | Schmaus et al. |
| 2007/0065383 A1 | 3/2007 | Fernandez De Castro |
| 2007/0065385 A1 | 3/2007 | Porter |
| 2007/0082039 A1 | 4/2007 | Jones, Jr. et al. |
| 2007/0138208 A1 * | 6/2007 | Scholz ................ A47K 5/1204 222/179 |
| 2007/0148101 A1 | 6/2007 | Synder et al. |
| 2007/0184013 A1 | 8/2007 | Synder et al. |
| 2007/0185216 A1 | 8/2007 | Synder et al. |
| 2007/0197704 A1 | 8/2007 | Walter et al. |
| 2007/0265352 A1 | 11/2007 | Roeding et al. |
| 2009/0004122 A1 | 1/2009 | Modak et al. |
| 2009/0018213 A1 | 1/2009 | Synder et al. |
| 2009/0082472 A1 | 3/2009 | Peters |
| 2009/0175806 A1 | 7/2009 | Modak et al. |
| 2009/0227675 A1 | 9/2009 | Lindstrom et al. |
| 2009/0238787 A1 | 9/2009 | Finke et al. |
| 2010/0068161 A1 | 3/2010 | Todary |
| 2010/0317743 A1 | 12/2010 | Macinga et al. |
| 2012/0129950 A1 | 5/2012 | Macinga et al. |

FOREIGN PATENT DOCUMENTS

| | | |
|---|---|---|
| EP | 1764135 A1 | 3/2007 |
| EP | 1769824 A1 | 4/2007 |
| EP | 1967576 A1 | 9/2009 |
| JP | 11322591 A | 11/1999 |
| JP | 2004352688 A | 12/2004 |
| JP | 2005526036 A | 9/2005 |
| JP | 2006273719 A | 10/2006 |
| JP | 2007145750 A | 6/2007 |
| JP | 2007532542 A | 11/2007 |
| JP | 2009517152 A | 4/2009 |
| KR | 1020080108972 A | 12/2008 |
| WO | 9956715 A1 | 11/1999 |
| WO | 03003998 A1 | 1/2003 |
| WO | 2005030917 A1 | 4/2005 |
| WO | 2005102276 A1 | 11/2005 |
| WO | 2006033970 A2 | 3/2006 |
| WO | 2007063065 A1 | 6/2007 |
| WO | 2007103687 A2 | 9/2007 |
| WO | 2008067028 A2 | 6/2008 |
| WO | 2008132621 A1 | 11/2008 |
| WO | 2008135085 A1 | 11/2008 |
| WO | 2009058802 A2 | 5/2009 |

OTHER PUBLICATIONS

Exam Report from Indian Application No. 9795/DELNP/2011 dated Jul. 26, 2017.

Notice for Reasons for Rejection for Japanese Patent Application No. 2012-516148 dated Jun. 23, 2014; and English Translation of said Rejection.

* cited by examiner

METHODS AND COMPOSITIONS FOR USE WITH GEL DISPENSERS

RELATED APPLICATIONS

This application is a continuation of U.S. patent application Ser. No. 15/198,083, filed on Jun. 30, 2016, which is a continuation of U.S. patent application Ser. No. 12/814,527, filed on Jun. 14, 2010, now U.S. Pat. No. 9,402,393, which claims the benefit of U.S. Provisional Ser. No. 61/187,041 filed on Jun. 15, 2009, the entire disclosures of which are incorporated herein by reference.

TECHNICAL FIELD

One or more embodiments of the present invention provide a method of reducing the frequency of mis-directed output of hydroalcoholic gel from a dispenser. A method of reducing the formation of coagulated gel deposits and dispensable hydroalcoholic gel compositions are also provided.

BACKGROUND OF THE INVENTION

Personal care and sanitizing compositions are often formulated as hydroalcoholic gels. Frequently, these products are provided in dispensers. Dispenser outlets such as nozzles can become clogged or partially blocked over time, due to the coagulation of gel creating a deposit on the nozzles. The clogged nozzle then causes mis-direction of the product when the dispenser is next used. Instead of dispensing product directly into the user's hand, product shoots from the clogged nozzle in a sideways fashion. Mis-directed product may hit walls, clothing, the floor, and can cause damage to these articles or areas. Therefore there remains a need for hydroalcoholic gel compositions that exhibit a reduced occurrence of clogging of dispenser nozzles.

SUMMARY OF THE INVENTION

One or more embodiments of this invention provides a method of reducing the frequency of mis-directed output from a gel dispenser, the method comprising the steps of combining a $C_{1-6}$ alcohol, an effective amount of a polyacrylate thickener; and a plug-preventing additive to form a dispensable gel composition; wherein said plug-preventing additive comprises a $C_{6-10}$ alkane diol; and wherein said composition comprises at least about 30 wt. % of said alcohol, based upon the total weight of the dispensable gel composition, and storing the dispensable gel in a pump-type dispenser that includes an outlet and that is activated on a periodic basis, wherein the frequency of mis-directed output is reduced when compared to a dispensable gel that does not include the plug-preventing additive.

In one or more embodiments, the present invention provides a method of reducing the formation of coagulated gel deposits, the method comprising the steps of combining a $C_{1-6}$ alcohol, an effective amount of a polyacrylate thickener; and a plug-preventing additive to form a dispensable gel composition; wherein said plug-preventing additive comprises a $C_{6-10}$ alkane diol; and wherein said composition comprises at least about 30 wt. % of said alcohol, based upon the total weight of the dispensable gel composition; and storing the dispensable gel in a pump-type dispenser that is activated on a periodic basis, wherein the formation of coagulated gel deposits is reduced when compared to a dispensable gel that does not include the plug-preventing additive.

In one or more embodiments, the present invention provides an hydroalcoholic gel composition comprising at least about 30 wt. % of a $C_{1-6}$ alcohol, based upon the total weight of the hydroalcoholic gel composition; an effective amount of a polyacrylate thickener; and a $C_{6-10}$ alkane diol.

DETAILED DESCRIPTION OF ILLUSTRATIVE EMBODIMENTS

In one or more embodiments, dispensable hydroalcoholic gel compositions of the present invention include a hydroalcoholic carrier, a polyacrylate thickener, and a plug-preventing additive. In one or more embodiments, the hydroalcoholic carrier includes water and alcohol.

In one embodiment, the alcohol is a lower alkanol, i.e. an alcohol containing 1 to 6 carbon atoms, in other embodiments 1 to 4 carbon atoms. Typically, these alcohols have antimicrobial properties. Examples of lower alkanols include, but are not limited to, methanol, ethanol, propanol, isopropanol, butanol, isobutanol, tertiary butanol, and mixtures thereof. In one embodiment, the alcohol comprises ethanol.

Generally, the hydroalcoholic gel composition comprises at least about 30 percent by weight (wt. %) alcohol, based upon the total weight of the hydroalcoholic gel composition. In one embodiment, the hydroalcoholic gel composition comprises at least about 35 wt. % alcohol, in another embodiment, the hydroalcoholic gel composition comprises at least about 40 wt. % alcohol, in another embodiment, the hydroalcoholic gel composition comprises at least about 50 wt. % alcohol, in another embodiment, the hydroalcoholic gel composition comprises at least about 60 wt. % alcohol, in another embodiment, the hydroalcoholic gel composition comprises at least about 65 wt. % alcohol, in yet another embodiment, the hydroalcoholic gel composition comprises at least about 70 wt. % alcohol, and in still yet another embodiment, the hydroalcoholic gel composition comprises at least about 78 wt. % alcohol, based upon the total weight of hydroalcoholic gel composition. More or less alcohol may be required in certain instances, depending particularly on other ingredients and/or the amounts thereof employed in the composition. In certain embodiments, the hydroalcoholic gel composition comprises from about 50 wt. % to about 98 wt. % alcohol, in other embodiments, the hydroalcoholic gel composition comprises from about 60 wt. % to about 95 wt. % of alcohol, in yet other embodiments, the hydroalcoholic gel composition comprises from about 65 wt. % to about 90 wt. % of alcohol, and in still other embodiments, the hydroalcoholic gel composition comprises from about 70 wt. % to about 85 wt. % of alcohol, based upon the total weight of the hydroalcoholic gel composition.

In one or more embodiments, the plug-preventing additive comprises one or more $C_{6-10}$ alkane diols, i.e. diols having a carbon chain length of 6 to 10. In one or more embodiments, the diol comprises a straight chain diol. In one or more embodiments, the diol includes 1,2-hexanediol, 1,2-octanediol, 1,9-nonanediol, 1,2-decanediol, 1,10-decanediol, or a mixture thereof 1,2-octanediol is sometimes referred to as caprylyl glycol. In one or more embodiments, the diol comprises one or more $C_{6-8}$ alkane diols, i.e. diols having a carbon chain length of 6 to 8.

In one embodiment, an effective amount of diol is at least about 0.05 wt. %, based upon the total weight of the hydroalcoholic gel composition, in another embodiment at least about 0.1, and in yet another embodiment at least about 0.15 wt. %, based upon the total weight of the hydroalcoholic gel composition.

Generally, an effective amount of diol is from about 0.05 to about 4 wt. %, based upon the total weight of the hydroalcoholic gel composition. In one embodiment, the diol is present in an amount of from about 0.1 to about 1 wt. %, in another embodiment, the diol is present in an amount of from about 0.15 to about 0.7 wt. %, in yet another embodiment, from about 0.2 to about 0.6 wt. %, and in still yet another embodiment, from about 0.25 to about 0.5 wt. %, based upon the total weight of the hydroalcoholic gel composition. It will be understood that greater amounts of diol can be employed, if desired, and are expected to perform at least equally as well.

In one embodiment, the diol plug-preventing additive is present in an amount of up to about 4 wt. % active, based upon the total weight of the hydroalcoholic gel composition. In another embodiment, the diol plug-preventing additive is present in an amount of up to about 1 wt. %, based upon the total weight of the hydroalcoholic gel composition, in yet another embodiment, the diol plug-preventing additive is present in an amount of up to about 0.7 wt. %, based upon the total weight of the hydroalcoholic gel composition, and in yet another embodiment, the diol plug-preventing additive is present in an amount of up to about 0.5 wt. %, based upon the total weight of the hydroalcoholic gel composition.

In certain embodiments, the diol is added to the hydroalcoholic gel composition as a solution or emulsion. In other words, the diol may be premixed with a carrier to form a diol solution or emulsion, with the proviso that the carrier does not deleteriously affect the sanitizing properties of the composition. Examples of carriers include water, alcohol, glycols such as propylene or ethylene glycol, ketones, linear and/or cyclic hydrocarbons, triglycerides, carbonates, silicones, alkenes, esters such as acetates, benzoates, fatty esters, glyceryl esters, ethers, amides, polyethylene glycols and PEG/PPG copolymers, inorganic salt solutions such as saline, and mixtures thereof. It will be understood that, when the diol is premixed to form a diol solution or emulsion, the amount of solution or emulsion that is added to the hydroalcoholic gel composition is selected so that the amount of diol falls within the ranges set forth hereinabove.

In one or more embodiments, the antimicrobial may be thickened with polyacrylate thickeners such as those conventionally available and/or known in the art. Examples of polyacrylate thickeners include carbomers, acrylates/C 10-30 alkyl acrylate crosspolymers, copolymers of acrylic acid and alkyl (C5 -C10) acrylate, copolymers of acrylic acid and maleic anhydride, and mixtures thereof.

In one or more embodiments, the polymeric thickener includes from about 0.5% to about 4% by weight of a cross-linking agent. Examples of cross-linking agents include the polyalkenyl polyethers.

Commercially available polymers of the polyacrylate type include those sold under the trade names Carbopol®, Acrysol® ICS-1, Polygel®, Sokalan®, Carbopol® 1623, Carbopol® 695, Ultrez 10, and Polygel® DB.

In one or more embodiments, the hydroalcoholic gel composition includes an effective amount of a polymeric thickener to adjust the viscosity of the hydroalcoholic gel to a viscosity range of from about 1000 to about 65,000 centipoise. In one embodiment, the viscosity of the hydroalcoholic gel is from about 5000 to about 35,000, and in another embodiment, the viscosity is from about 10,000 to about 25,000. The viscosity is measured by a Brookfield RV Viscometer using RV and/or LV Spindles at 22° C.+/−3° C.

As will be appreciated by one of skill in the art, the effective amount of thickener will vary depending upon a number of factors, including the amount of alcohol and other ingredients in the hydroalcoholic gel composition. In one or more embodiments, an effective amount of thickener is at least about 0.01 wt. %, based upon the total weight of the hydroalcoholic gel composition. In other embodiments, the effective amount is at least about 0.02 wt. %, in yet other embodiments at least about 0.05 wt. %, and it still other embodiments, at least about 0.1 wt. %. In one embodiment, the effective amount of thickener is at least about 0.5 wt. %, and in another embodiment, at least about 0.75 wt. %, based upon the total weight of the hydroalcoholic gel. In one or more embodiments, the compositions according to the present invention comprise up to about 10% by weight of the total composition of a polymeric thickener. In certain embodiments, the amount of thickener is from about 0.01 to about 1 wt. %, in another embodiment, from about 0.02 to about 0.4 wt. %, and in another embodiment, from about 0.05 to about 0.3 wt. %, based upon the total weight of the hydroalcoholic gel. In one embodiment, the amount of thickener is from about 0.1 to about 10 wt. %, in another embodiment from about 0.5% to about 5% by weight, in another embodiment from about 0.75% to about 2% wt. %, based upon the total weight of the hydroalcoholic gel.

In one or more embodiments, the hydroalcoholic gel may further comprise a neutralizer. The use of neutralizing agents to form salts of carbomer polymers is known. Examples of neutralizing agents include amines, alkanolamines, alkanolamides, inorganic bases, amino acids, including salts, esters and acyl derivatives thereof.

Examples of common neutralizers are shown in Table 1, along with the manufacturers of these neutralizers, and the suggested ratio (per one part polymeric thickener) to achieve neutralization (pH 7.0) when the polymeric thickener has an equivalent weight of about 76+/−4.

TABLE 1

| Trade Name | CTFA Name | Manufacturer | Neutralization Ratio Base/ Carbopol ® Polymer |
|---|---|---|---|
| NaOH (18%) | Sodium Hydroxide | | 2.3/1.0 |
| Ammonia (28%) | Ammonium Hydroxide | | 0.7/1.0 |
| KOH (18%) | Potassium Hydroxide | | 2.7/1.0 |
| L-Arginine | Arginine | Ajinomoto | 4.5/1.0 |
| AMP-95 ® | Aminomethyl Propanol | Angus | 0.9/1.0 |
| Neutrol ® TE | Tetrahydroxypropyl Ethylenediamine | BASF | 2.3/1.0 |
| TEA (99%) | Triethanolamine | | 1.5/1.0 |
| Tris Amino ® (40%)* | Tromethamine | Angus | 3.3/1.0 |
| Ethomeen ® C-25 | PEG 15 Cocamine | Akzo | 6.2/1.0 |
| Diisopropanol-amine | Diisopropanol-amine | Dow | 1.2/1.0 |
| Triisopropanol-amine | Triisopropanol-amine | Dow | 1.5/1.0 |

In one or more embodiments, the neutralizer may be selected based on the amount of alcohol that is to be gelled. Table 2 shows commonly recommended neutralizers for hydroalcoholic systems.

TABLE 2

| Up to % Alcohol | Neutralizer |
| --- | --- |
| 20% | Sodium Hydroxide |
| 30% | Potassium Hydroxide |
| 60% | Triethanolamine |
| 60% | Tris Amino |
| 80% | AMP-95 ® |
| 90% | Neutrol TE |
| 90% | Diisopropanolamine |
| 90% | Triisopropanolamine |
| >90 | Ethomeen C-25 |

As stated hereinabove, gel products may be provided in dispensers. The type of dispenser is not limited, and may include portable pump bottles. Dispenser outlets such as nozzles can become clogged or partially blocked over time, due to the coagulation of gel creating a deposit on the nozzles. The clogged nozzle may then cause mis-direction of the product when the dispenser is next used. Advantageously, it has been found that $C_{6-10}$ alkane diols are effective plug-preventing additives for hydroalcoholic gel products. In one or more embodiments, antimicrobial hydroalcoholic gel containing a $C_{6-10}$ alkane diol plug-preventing additive exhibits less misdirection upon being dispensed than do hydroalcoholic gels that do not contain a plug-preventing agent. In one or more embodiments, the additive prevents the hydroalcoholic gel from coagulating into solid or semi-solid material that may deposit onto a surface or plug a dispenser nozzle.

As described hereinabove, the hydroalcoholic gel composition of this invention includes a thickened hydroalcoholic gel and a plug-preventing additive. The composition can further comprise a wide range of optional ingredients, with the proviso that they do not deleteriously affect the sanitizing efficacy of the composition, or the frequency of mis-directed dispenser output. With respect to sanitizing efficacy, deleterious should be interpreted to mean that the decrease in the log reduction according to the FDA TFM healthcare personnel hand wash test is not de minimus, or in other words, the log reduction does not decrease by more than about 0.5. With respect to mis-direction, deleterious should be interpreted to mean that the optional ingredients do not increase the frequency of mis-directed dispenser output by more than about 5 percent.

The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Nonlimiting examples of functional classes of ingredients are described at page 537 of this reference. Examples of these functional classes include: abrasives, anti-acne agents, anti-caking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, humectants, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

In certain embodiments, the hydroalcoholic gel composition comprises one or more humectants. Examples of humectants include propylene glycol, dipropyleneglycol, hexylene glycol, 1,4-dihydroxyhexane, 1,2,6-hexanetriol, sorbitol, butylene glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, lactic acid, sodium pyrrolidone carboxylic acid, hyaluronic acid, chitin, and the like. In one embodiment, the humectant is present in an amount of from about 0.1 to about 20% by weight, based upon the total weight of the hydroalcoholic gel composition. In another embodiment the humectant is present in an amount of from about 1 to about 8% by weight, in another embodiment from about 2 to about 3% by weight, based upon the total weight of the hydroalcoholic gel composition.

In these or other embodiments, the hydroalcoholic gel composition comprises one or more conditioning or moisturizing esters. Examples of esters include cetyl myristate, cetyl myristoleate, and other cetyl esters, diisopropyl sebacate, and isopropyl myristate. In one embodiment, the ester is present in an amount of up to 10% by weight, based upon the total weight of the hydroalcoholic gel composition. In another embodiment the ester is present in an amount of from about 0.5 to about 5% by weight, in another embodiment from about 1 to about 2% by weight, based upon the total weight of the hydroalcoholic gel composition.

In one or more embodiments, the hydroalcoholic gel composition includes one or more emulsifying agents. Examples of emulsifying agents include stearyl alcohol, sorbitan oleate trideceth-2, poloxamers, and PEG/PPG-20/6 dimethicone. In one embodiment, the emulsifying agent is present in an amount of up to about 10% by weight, based upon the total weight of the hydroalcoholic gel composition. In another embodiment the emulsifying agent is present in an amount of from about 0.1 to about 5% by weight, in another embodiment from about 0.5 to about 2% by weight, based upon the total weight of the hydroalcoholic gel composition.

In one embodiment, the hydroalcoholic gel composition includes one or more thickeners and optionally one or more stabilizers. Examples of thickeners and stabilizers include hydroxyethyl cellulose hydroxypropyl cellulose, methyl cellulose, carboxymethyl cellulose, and ammonium acryloyldimethyltaurate/VP copolymer. In one embodiment, where the thickener or stabilizer is starch-based, the thickener or stabilizer is present in an amount of up to about 10% by weight, in another embodiment in an amount of from about 0.1 to about 5% by weight, in yet another embodiment from about 0.2 to about 1% by weight, based upon the total weight of the hydroalcoholic gel composition. In other embodiments, where the thickener or stabilizer is a synthetic polymer, the thickener or stabilizer is present in an amount of up to about 15% by weight, in another embodiment in an amount of from about 0.1 to about 10% by weight, in yet another embodiment from about 1 to about 2% by weight, based upon the total weight of the hydroalcoholic gel composition.

In one or more embodiments, the hydroalcoholic gel composition includes one or more solubilizers. Examples of solubilizers include PEG-40 hydrogenated castor oil, polysorbate-80, PEG-80 sorbitan laurate, ceteareth-20, oleth-20, PEG-4, and propylene glycol. The amount of solubilizer is not particularly limited, so long as it does not deleteriously affect the sanitizing efficacy of the composition.

In one or more embodiments, the hydroalcoholic gel composition includes one or more antiviral agents or antiviral enhancers. Examples of antiviral agents include botanicals such as rosmarinic acid, tetrahydrocurcuminoids, oleuropen, oleanolic acid, aspalathus linearis extract, white tea, red tea, green tea extract, neem oil limonoids, coleus oil, licorice extract, burnet, ginger & cinnamon extracts, alpha-glucan oligosaccharide, perilla ocymoides leaf powder, camphor, camellia oleifera leaf extract, ginger, menthol, eucalyptus, capillisil hc, hydroxyprolisilane cn, sandlewood oil/resin, calendula oil, rosemary oil, lime/orange oils, and hop acids. When used, the antiviral agents are present in amounts of from about 0.1 to about 1 percent by weight, based upon the total weight of the hydroalcoholic gel composition.

Examples of antiviral enhancers include proton donors, cationic oligomers and polymers, chaotropic agents, and copper and zinc compounds. Antiviral enhancers are further described in co-pending U.S. Patent Application Publications 2007/0184013, 2007/0185216, and 2009/0018213, all of which are hereby incorporated by reference.

In certain embodiments, the hydroalcoholic gel composition does not contain any auxiliary antimicrobial ingredients. Any antimicrobial ingredient other than the alcohol may be referred to as an auxiliary antimicrobial agent. In one embodiment, the amount of auxiliary antimicrobial agent (including preservatives) is less than about 0.1 wt. %, in another embodiment, less than about 0.05 wt. %, based upon the total weight of the hydroalcoholic gel composition. In another embodiment, the hydroalcoholic gel composition is devoid of auxiliary antimicrobial agents.

It is envisioned that, in other embodiments, auxiliary antimicrobial agents could be included, with the proviso that the antimicrobial ingredient does not deleteriously affect the sanitizing properties of the composition. Examples of auxiliary antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methylhexahydropyrimidine; chlorhexidine salts including chlorhexidine gluconate and the salts of N,N"-Bis(4-chlorophenyl)-3,12-diimino-2,4,11,14-tetraazatetradecanediimidi amide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quaternium-15 and available from Dow Chemical Company under the tradename DOWCIL™ 2000; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, tropolone, and mixtures thereof. When used, the auxiliary antimicrobial agents are present in amounts of from about 0.1 to about 1 wt. %, based upon the total weight of the hydroalcoholic gel composition.

Advantageously, certain ingredients that have been designated as critical to current antiseptic compositions can be limited in the hydroalcoholic gel composition of the present invention. For example, zinc compounds such as organic salts of zinc, zinc gluconate, zinc pyrithione, or zinc omadine are not necessary, and can be limited, if desired, to less than about 0.5 wt. %, or in another embodiment to less than about 0.1 wt. %, or in another embodiment to less than about 0.05 wt. %, based upon the total weight of the hydroalcoholic gel composition. In another embodiment, the hydroalcoholic gel composition is devoid of organic salts of zinc.

In one or more embodiments, the amount of acid may be limited. More specifically, in one or more embodiments, the amount of organic acid may be limited. In one or more embodiments, the amount of any of the following acids may be limited: citric acid, glycolic acid, lactic acid, malic acid, tartaric acid, and acetic acid. When limited, in one or more embodiments, the amount of acid may be less than 0.125 wt. %, in other embodiments less than about 0.08 wt. %, based upon the total weight of the hydroalcoholic gel composition. In another embodiment, the hydroalcoholic gel composition is devoid of citric acid, glycolic acid, lactic acid, malic acid, tartaric acid, and acetic acid.

In one or more embodiments, the amount of essential oil is less than 0.1 wt. %, or in another embodiment less than about 0.05 wt. %, based upon the total weight of the hydroalcoholic gel composition. In another embodiment, the hydroalcoholic gel composition is devoid of essential oils. More specifically, in one embodiment, the hydroalcoholic gel composition contains less than 0.1 wt. %, in another embodiment less than 0.05, and in another embodiment, is devoid of any of the following essential oils: cinnamon oil, basil oil, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, eucalyptus oil, lemon oil, orange oil, sweet orange oil, and calendula oil, wherein the above amounts are based upon the total weight of the hydroalcoholic gel composition.

In one or more embodiments, the amount of specific constituents of essential oils is also limited. More specifically, in one embodiment, the hydroalcoholic gel composition contains less than 0.1 wt. %, in another embodiment less than 0.05, and in another embodiment, is devoid of any of the following constituents of essential oils: farnesol, nerolidol, bisabolol, apritone, chamazulene, santalol, zingiberol, carotol, and caryophyllen, curcumin, 1-citronellol, a-amyl-cinnarnaldehyde, lyral, geraniol, farnesol, hydroxycitronellal, isoeugenol, eugenol, camphor, eucalyptol, linalool, citral, thymol, limonene and menthol, wherein the above amounts are based upon the total weight of the hydroalcoholic gel composition.

In one or more embodiments, the hydroalcoholic gel composition is devoid of traditional preservative agents. Traditional preservative agents include parabens, benzoic acid, potassium sorbate, iodopropynyl butylcarbomate, tropolone, dibromodicyanobutane, 1,2-benziosthiazolin-3-one, and phenoxyethanol. In one or more embodiments, the amount of glycerin is less than about 20 wt. %, in other embodiments, less than about 15 wt. %, in yet other embodiments, less than about 10 wt. %, based upon the total weight of the hydroalcoholic gel composition. Indeed, any component other than the thickened hydroalcoholic gel and the diol plug-preventing additive is not necessary and can optionally be limited to less than about 0.5 wt. %, if desired to less than about 0.1 wt. %, if desired to less than about 0.01 wt. %, or if desired to less than about 0.001 wt. %.

In one or more embodiments, the balance of the hydroalcoholic gel composition includes water or other suitable solvent. In one embodiment, one or more volatile silicone-based materials are included in the formulation to further aid the evaporation process. Exemplary volatile silicones have a lower heat of evaporation than alcohol. In certain embodiments, use of silicone-based materials can lower the surface tension of the fluid composition. This provides greater contact with the surface. In one embodiment, the silicone-based material, such as cyclomethicone, trimethylsiloxy silicate or a combination thereof, may be included in the formulation at a concentration of from about 4 wt. % to about 50 wt. % and in another embodiment from about 5 wt. % to about 35 wt. %, and in yet another embodiment from about 11 wt. % to about 25 wt. %, based upon the total weight of the hydroalcoholic gel composition. In one embodiment, the hydroalcoholic gel composition is devoid of any component other than alcohol, thickener, neutralizer, diol plug-preventing additive and optionally water or other suitable solvent.

The dispensable hydroalcoholic gel composition may be prepared by simply mixing the components together. The hydroalcoholic gel composition may be prepared by simply mixing the components together. In one embodiment, where one or more components is obtained as a solid powder, the hydroalcoholic gel composition is prepared by a method comprising dispersing the solid powder in water to form a gel, adding alcohol with slow to moderate agitation, and then adding other ingredients as desired, and mixing until the mixture is homogeneous. The order of addition is not particularly limited. In one embodiment, the hydroalcoholic gel composition is prepared by a method comprising dispersing the polymeric thickener in alcohol with slow to moderate agitation, adding water, and then adding a plug-preventing additive, and mixing until the mixture is homogeneous. In other embodiments, the hydroalcoholic gel composition is prepared by a method comprising dispersing the polymeric thickener in water with slow to moderate agitation, adding alcohol, a plug-preventing additive, and mixing until the mixture is homogeneous. In one or more embodiments, a neutralizer is added to the mixture to neutralize the thickener and form the gel. Those of skill in the art will understand that optional ingredients may be added at various points during the mixing process. It will also be understood that a gel may be formed without a neutralizer if the thickener is one that swells when mixed with water or alcohol.

In one embodiment, where the hydroalcoholic gel composition is in liquid form, the percent solids of the hydroalcoholic gel composition is less than about 6 percent, in another embodiment, less than about 5 percent, in yet another embodiment, less than about 4 percent, in still another embodiment, less than about 3 percent, in another embodiment, less than about 2 percent, in yet another embodiment, less than about 1 percent. The percent solids can be determined by various methods known in the art.

In one or more embodiments, the pH of the hydroalcoholic gel composition is from about 1.5 to about 10, in another embodiment from about 4.5 to about 9.5, in another embodiment from about 7 to about 8.

The hydroalcoholic gel composition of the present invention may be employed in any type of dispenser typically used for gel products, for example pump dispensers. A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT® and TFX™ as well as traditional bag-in-box dispensers. Examples of dispensers are described in U.S. Pat. Nos. 5,265,772, 5,944,227, 6,877,642, 7,028,861, and U.S. Published Application Nos. 2006/0243740 A1 and 2006/0124662 A1, all of which are incorporated herein by reference. In one or more embodiments, the dispenser includes an outlet such as a nozzle, through which the hydroalcoholic gel composition is dispensed.

In one or more embodiments, the hydroalcoholic gel of the present invention prevents the mess that occurs from mis-directed dispenser output. The hydroalcoholic gel is more likely to be effective, because it is more likely that an effective amount of the gel will be dispensed onto the target surface. Less product is wasted and user satisfaction is higher.

In one or more embodiments, the hydroalcoholic gel of the present invention exhibited less misdirection upon being dispensed than did common hydroalcoholic gels that did not contain an plug-preventing agent. Frequency of mis-directed output may be determined as a percentage of total dispenser actuations. Comparative measurements may be taken at various rates of actuation. An output target may be created to distinguish between acceptable output and mis-directed output. In one or more embodiments, the output target simulates the hand(s) of the dispenser user. The output target defines a zone of acceptable output.

In one or more embodiments, when an effective amount of a diol plug-preventing additive is added to a hydroalcoholic gel composition, the frequency of mis-directed output may be reduced. In certain embodiments, the dispenser output will be outside of a 2.5 inch square zone about 3 inches directly below the dispenser nozzle with less than 50% frequency when the rate of dispenser actuation is 0.1 actuations per hour. In other embodiments, the dispenser output will be outside of a 2.5 inch square zone about 3 inches directly below the dispenser nozzle with less than 30% frequency when the rate of dispenser actuation is 0.1 actuations per hour. In one or more embodiments, the dispenser output will be outside of a 2.5 inch square zone about 3 inches directly below the dispenser nozzle with less than 20% frequency when the rate of dispenser actuation is 0.1 actuations per hour. In one embodiment, the dispenser output will be outside of a 2.5 inch square zone about 3 inches directly below the dispenser nozzle with less than 15% frequency when the rate of dispenser actuation is 0.1 actuations per hour.

In certain embodiments, the dispenser output will be outside of a 2.5 inch square zone about 3 inches directly below the dispenser nozzle with less than 10% frequency when the rate of dispenser actuation is 0.1 actuations per hour. In other embodiments, the dispenser output will be outside of a 2.5 inch square zone about 3 inches directly below the dispenser nozzle with less than 5% frequency when the rate of dispenser actuation is 0.1 actuations per hour. In one or more embodiments, the dispenser output will be outside of a 2.5 inch square zone about 3 inches directly below the dispenser nozzle with less than 1% frequency when the rate of dispenser actuation is 0.1 actuations per hour. In one embodiment, the dispenser output will be outside of a 2.5 inch square zone about 3 inches directly below the dispenser nozzle with less than 0.5% frequency when the rate of dispenser actuation is 0.1 actuations per hour. In one or more embodiments, substantially none of the dispenser output will be outside of a 2.5 inch square zone about 3 inches directly below the dispenser nozzle when the rate of dispenser actuation is 0.1 actuations per hour.

In certain embodiments, the dispenser output will be outside of a 2.5 inch square zone about 3 inches directly below the dispenser nozzle with less than 40% frequency when the rate of dispenser actuation is 0.5 actuations per hour. In other embodiments, the dispenser output will be outside of a 2.5 inch square zone about 3 inches directly below the dispenser nozzle with less than 30% frequency when the rate of dispenser actuation is 0.5 actuations per hour. In one or more embodiments, the dispenser output will be outside of a 2.5 inch square zone about 3 inches directly below the dispenser nozzle with less than 20% frequency when the rate of dispenser actuation is 0.5 actuations per hour. In one embodiment, the dispenser output will be outside of a 2.5 inch square zone about 3 inches directly below the dispenser nozzle with less than 15% frequency when the rate of dispenser actuation is 0.5 actuations per hour.

In certain embodiments, the dispenser output will be outside of a 2.5 inch square zone about 3 inches directly below the dispenser nozzle with less than 10% frequency when the rate of dispenser actuation is 0.5 actuations per hour. In other embodiments, the dispenser output will be outside of a 2.5 inch square zone about 3 inches directly below the dispenser nozzle with less than 5% frequency when the rate of dispenser actuation is 0.5 actuations per hour. In one or more embodiments, the dispenser output will be outside of a 2.5 inch square zone about 3 inches directly below the dispenser nozzle with less than 1% frequency when the rate of dispenser actuation is 0.5 actuations per hour. In one embodiment, the dispenser output will be outside of a 2.5 inch square zone about 3 inches directly below the dispenser nozzle with less than 0.5% frequency when the rate of dispenser actuation is 0.5 actuations per hour. In one or more embodiments, substantially none of the dispenser output will be outside of a 2.5 inch square zone about 3 inches directly below the dispenser nozzle when the rate of dispenser actuation is 0.5 actuations per hour.

In certain embodiments, the dispenser output will be outside of a 2.5 inch square zone about 3 inches directly below the dispenser nozzle with less than 40% frequency when the rate of dispenser actuation is 3 actuations per hour. In other embodiments, the dispenser output will be outside of a 2.5 inch square zone about 3 inches directly below the dispenser nozzle with less than 30% frequency when the rate of dispenser actuation is 3 actuations per hour. In one or more embodiments, the dispenser output will be outside of a 2.5 inch square zone about 3 inches directly below the dispenser nozzle with less than 20% frequency when the rate of dispenser actuation is 3 actuations per hour. In one embodiment, the dispenser output will be outside of a 2.5 inch square zone about 3 inches directly below the dispenser nozzle with less than 15% frequency when the rate of dispenser actuation is 3 actuations per hour.

In certain embodiments, the dispenser output will be outside of a 2.5 inch square zone about 3 inches directly below the dispenser nozzle with less than 10% frequency when the rate of dispenser actuation is 3 actuations per hour. In other embodiments, the dispenser output will be outside of a 2.5 inch square zone about 3 inches directly below the dispenser nozzle with less than 5% frequency when the rate of dispenser actuation is 3 actuations per hour. In one or more embodiments, the dispenser output will be outside of a 2.5 inch square zone about 3 inches directly below the dispenser nozzle with less than 1% frequency when the rate of dispenser actuation is 3 actuations per hour. In one embodiment, the dispenser output will be outside of a 2.5 inch square zone about 3 inches directly below the dispenser nozzle with less than 0.5% frequency when the rate of dispenser actuation is 3 actuations per hour. In one or more embodiments, substantially none of the dispenser output will be outside of a 2.5 inch square zone about 3 inches directly below the dispenser nozzle when the rate of dispenser actuation is 3 actuations per hour.

In one or more embodiments, the effectiveness of the plug-preventing additive may be expressed in terms of the percent reduction in the frequency of misdirection. That is, a hydroalcoholic gel composition containing a plug-preventing additive may be tested in comparison to a control that does not contain a plug-preventing additive. The frequency of misdirection may be determined as described hereinabove, and the percent reduction in frequency of misdirection may be calculated for the composition containing the plug-preventing additive compared to the control. More generally, the percent reduction in the frequency of misdirection may be calculated for any rate of actuation and any output target zone relative to a control composition that does not contain any plug-preventing additive and is tested under the same conditions. In one or more embodiments, the percent reduction in the frequency of misdirection is at least about 50%. In other embodiments, the percent reduction in the frequency of misdirection is at least about 60%, in yet other embodiments, at least about 70% in still other embodiments, at least about 80%. In one or more embodiments, the percent reduction in the frequency of misdirection is at least about 90%, in other embodiments, at least about 95%, and in yet other embodiments, at least about 97%.

In order to demonstrate the practice of the present invention, the following examples have been prepared and tested. The examples should not, however, be viewed as limiting the scope of the invention. The claims will serve to define the invention.

EXAMPLES

Examples 1 and 2 are hydroalcoholic gel formulations that contain about 70 wt. % ethanol. They also each contain the same amount of the following ingredients: Acrylates/C10-30 alkyl acrylate crosspolymer, glycerin, aminomethyl propanol, and water. Example 1 differs from Example 2 in that Example 2 also contains 1 wt. % of 1,2-octanediol. Examples 1 and 2 were dispensed by using a GOJO NXT® side-by-side dispenser with 1000 ml refills and DPI pumps. The dispenser is ADA compliant, and features one-hand push operation. The rate of actuations was held constant for all samples. The output target zone was positioned about 3 inches below the nozzle tip, and was defined by a 2.5 inch square.

The tests were performed over 15 days, and the frequency of mis-direction was calculated as a percentage of misdirected outputs based upon the total number of actuations for each composition. Each sample was tested in multiple dispensers, and the results were averaged, and are summarized in the Table below. Approximately 900 actuations were observed for each formulation. The reduction in frequency of mis-direction was also calculated for Example 2, as compared to Example 1. Where the frequency of misdirection was relatively high, deposits of coagulated gel were observed on surfaces of the dispenser nozzle.

TABLE 3

| EXAMPLE | % MIS-DIRECTION | % REDUCTION |
|---|---|---|
| 1 | 34.89 | N/A |
| 2 | 5.67 | 83.75 |

In one or more embodiments, the compositions of the present invention exhibit good moisturizing properties, and dispenser clogging and mis-directed output is reduced.

In one or more embodiments, the hydroalcoholic gel composition of this invention provides good product stability over a long-term shelf life. In certain embodiments, the stability of the hydroalcoholic gel compositions of the present invention is better than the stability of products that are emulsions or solid suspensions. Product stability includes physical properties such as stable viscosity and pH readings over time. Also, product stability requires that the products retain a uniform consistency and appearance, and color and odor must not significantly change so that aged product is different from freshly manufactured product. In one or more embodiments, the hydroalcoholic gel compositions of the present invention exhibit good product stability over a shelf-life of about three years.

Various modifications and alterations that do not depart from the scope and spirit of this invention will become apparent to those skilled in the art. This invention is not to be duly limited to the illustrative embodiments set forth herein.

What is claimed is:

1. A dispensable gel composition comprising:
    at least 50 wt. % of a $C_{1-4}$ alcohol, based upon the total weight of the dispensable gel composition;
    from 0.01 to 10 wt. % of a polyacrylate thickener, based upon the total weight of the dispensable gel composition; and
    from 0.05 to 4 wt. % of a plug-preventing additive, based upon the total weight of the dispensable gel composition, wherein said plug-preventing additive is a $C_{6-10}$ alkane diol,
    wherein the frequency of mis-directed output is reduced by at least 50% during dispensing from a dispensing device as compared to another dispensable gel composition that is otherwise identical to said dispensable gel composition except that it does not include the plug-preventing additive.

2. The dispensable gel composition of claim 1, wherein the $C_{1-4}$ alcohol is selected from the group consisting of ethanol, propanol, isopropanol, butanol, isobutanol, tertiary butanol, methanol, and mixtures thereof.

3. The dispensable gel composition of claim 2, wherein the plug-preventing additive is 1,2-octanediol, 1,2-hexanediol, 1,9-nonanediol, 1,2-decanediol, 1,10-decanediol, or a mixture thereof.

4. The dispensable gel composition of claim 3, wherein the polyacrylate thickener is selected from the group consisting of acrylates/C 10-30 alkyl acrylate crosspolymers, copolymers of acrylic acid and alkyl C5-C10 acrylate, copolymers of acrylic acid and maleic anhydride, carbomers, and mixtures thereof.

5. The dispensable gel composition of claim 1, wherein the plug-preventing additive is 1,2-octanediol, and wherein the 1,2-octanediol is present in an amount of from 0.1 to 1 wt. %, based upon the total weight of the dispensable gel composition.

6. The dispensable gel composition of claim 1, wherein the dispensable gel composition has a viscosity of from 1,000 to 65,000 centipoise, when measured using RV or LV spindles at 22° C.

7. The dispensable gel composition of claim 1, wherein the $C_{6-10}$ alkane diol is present in an amount of from 0.15 to 0.7 wt. %, based upon the total weight of the dispensable gel composition.

8. The dispensable gel composition of claim 1, wherein the $C_{6-10}$ alkane diol is present in an amount of from 0.2 to 0.6 wt. %, based upon the total weight of the dispensable gel composition.

9. The dispensable gel composition of claim 1, wherein the $C_{6-10}$ alkane diol is 1,2-octane diol.

10. The dispensable gel composition of claim 9, wherein the dispensable gel composition comprises at least 60 wt. % of said $C_{1-4}$ alcohol.

11. The dispensable gel composition of claim 10, wherein the polyacrylate thickener is a carbomer.

\* \* \* \* \*